(12) United States Patent
Jhoti et al.

(10) Patent No.: US 7,149,280 B2
(45) Date of Patent: Dec. 12, 2006

(54) SYNTHESIS AND SCREENING OF LIGANDS USING X-RAY CRYSTALLOGRAPHY

(75) Inventors: Harren Jhoti, Cambridge (GB); Miles Stuart Congreve, Cambridge (GB); Marc O'Reilly, Cambridge (GB); Paul Graham Wyatt, Cambridge (GB)

(73) Assignee: Astex Therapeutics Limited, Cambridge (GB)

( * ) Notice: Subject to any disclaimer, the term of this patent is extended or adjusted under 35 U.S.C. 154(b) by 0 days.

(21) Appl. No.: 10/539,447

(22) PCT Filed: Dec. 22, 2003

(86) PCT No.: PCT/GB03/05595

§ 371 (c)(1),
(2), (4) Date: Aug. 30, 2005

(87) PCT Pub. No.: WO2004/057340

PCT Pub. Date: Jul. 8, 2004

(65) Prior Publication Data

US 2006/0159226 A1    Jul. 20, 2006

Related U.S. Application Data

(60) Provisional application No. 60/435,349, filed on Dec. 23, 2002.

(30) Foreign Application Priority Data

Dec. 24, 2002   (GB) ................................. 0230172.9

(51) Int. Cl.
*G01N 23/207*   (2006.01)
*G01N 23/20*    (2006.01)
*G01N 33/53*    (2006.01)

(52) U.S. Cl. ............................. 378/73; 378/71; 435/7.1

(58) Field of Classification Search ............ 378/70–74; 435/7.1, 447; 436/518
See application file for complete search history.

(56) References Cited

U.S. PATENT DOCUMENTS

| | | | |
|---|---|---|---|
| 5,958,702 A | 9/1999 | Benner | |
| 6,297,021 B1 | 10/2001 | Nienaber et al. | |
| 6,350,747 B1 | 2/2002 | Glennon et al. | |
| 6,950,757 B1 * | 9/2005 | Stewart | 702/27 |
| 7,079,621 B1 * | 7/2006 | Blomsma et al. | 378/73 |
| 2002/0054663 A1 * | 5/2002 | Olson et al. | 378/79 |
| 2002/0197628 A1 * | 12/2002 | Stewart | 435/6 |

FOREIGN PATENT DOCUMENTS

| | | |
|---|---|---|
| EP | 1 130 009 | 9/2001 |
| EP | 1 184 359 | 3/2002 |
| EP | 1 188 769 | 3/2002 |
| WO | WO 97/43232 | 11/1997 |
| WO | WO 99/15500 | 4/1999 |
| WO | 99/45379 | 9/1999 |
| WO | WO 99/45379 | 9/1999 |
| WO | WO 99/45389 | 9/1999 |
| WO | WO 99/49314 | 9/1999 |
| WO | WO 00/00823 | 1/2000 |
| WO | WO 00/39585 | 7/2000 |
| WO | WO 01/64605 | 9/2001 |
| WO | WO 02/20435 | 3/2002 |
| WO | WO 02/42773 | 5/2002 |
| WO | WO 02/077270 | 10/2002 |
| WO | WO 03/033437 | 4/2003 |
| WO | WO 03/034071 | 4/2003 |
| WO | WO 03/086612 | 10/2003 |

OTHER PUBLICATIONS

Cousins et al, Chem. Commun., 1999, vol. 16, pp. 1575-1576.
Nguyen et al, Chemical Communications, 2003, vol. 8, pp. 942-943.
Babine et al, Letters in Drug Design & Discovery, 2004, vol. 1(2), pp. 173-177.
Lindstrom, Chemical Reviews, 2002, vol. 102(8), pp. 2751-2771.
Eliseev et al, Chem. Eur. J., 1998, vol. 4, No. 5, pp. 825-834.
Rowan et al, J. Am. Chem. Soc., 1997, vol. 119, pp. 2578-2579.
Ramstrom et al, Nature Reviews Drug Discovery, 2002, vol. 1, pp. 26-36.
Bourne et al, PNAS, 2004, vol. 101, No. 6, pp. 1449-1454.
Choong et al, J. Med. Chem., 2002, vol. 45, pp. 5005-5022.
DeLano et al, Science, 2000, vol. 287, pp. 1279-1283.
Erlanson et al, PNAS, 2000, vol. 97, No. 17, pp. 9367-9372.
Maly et al, PNAS, 2000, vol. 97, No. 6, pp. 2419-2424.
Verlinde et al, In Structure-Based Drug Design (Veerapandian, P., ed.), 1997, pp. 365-394.
Verlinde et al, Journal of Computer-Aided Molecular Design, 1992, vol. 6, pp. 131-147.

(Continued)

Primary Examiner—Edward J. Glick
Assistant Examiner—Irakli Kiknadze
(74) Attorney, Agent, or Firm—Nixon & Vanderhye P.C.

(57) ABSTRACT

A method for identifying a ligand of a target macromolecule is disclosed, comprising the steps of: soaking one or more crystals of the target macromolecule in a solution containing a collection of compounds generated in situ or separate from the crystal, where the solution has been prepared without the purification of the synthesized collection of compounds; obtaining an X-ray crystal diffraction pattern of the soaked macromolecule crystal; and using said X-ray crystal diffraction pattern to identify any compound bound to the macromolecule crystal, said compound being a ligand of the target macromolecule.

12 Claims, No Drawings

OTHER PUBLICATIONS

Nienaber et al, Nature Biotechnology, 2000, vol. 18(10), pp. 1105-1108.
Katz et al, Biochemistry, 1995, vol. 34, pp. 8264-8280.
Katz et al, Nature, 1998, vol. 391, pp. 608-612.
Bunyapaiboonsri et al, Chembiochem, 2001, vol. 2, pp. 438-444.
Otto et al, Current Opinion in Chemical Biology, 2002, vol. 6, pp. 321-327.
Lehn et al, Science, 2001, vol. 291, pp. 2331-2332.
Cousins et al, Current Opinion in Chemical Biology, 2000, vol. 4, pp. 270-279.
Karan et al, DDT, 2000, vol. 5, No. 2, pp. 67-75.
Klekota et al, Trends Biotechnol., 1999, vol. 17, pp. 205-209.
Lehn, Chem. Eur. J., 1999, vol. 5, No. 9, pp. 2455-2463.
Ganesan, Angew. Chem. Int. Ed. 1998, vol. 37, No. 20, pp. 2828-2831.
Otto et al, DDT, 2002, vol. 7, No. 2, pp. 117-125.
Berl et al, Chem. Eur. J., 2000, vol. 6, No. 11, pp. 1938-1946.
Berl et al, Eur. J. Org. Chem., 1999, pp. 3089-3094.
Brady et al, Chem. Commun., 1996, pp. 319-320.
Erlanson et al, Nature Biotechnology, 2003, vol. 21, pp. 308-314.
Congreve et al, Angew. Chem. Int. Ed., 2003, vol. 42(37), pp. 4479-4482.
Eksterowicz et al, Journal of Molecular Graphics and Modelling, 2002, vol. 20, pp. 469-477.
Carr et al, DDT, 2002, vol. 7, No. 9, pp. 522-527.
Nguyen et al, Angew. Chem. Int. Ed., 2001, vol. 40, No. 9, pp. 1774-1776.
Lewis et al, Angew. Chem. Int. Ed., 2002, vol. 41, No. 6, pp. 1053-1057.
Huc et al, Combinatorial Chemistry & High Throughput Screening, 2001, pp. 109-130.
Huc et al, Eur. J. Inorg. Chem., 1999, pp. 1415-1420.
Huc et al, Proc. Natl. Acad. Sci., 1997, vol. 94, pp. 2106-2110.
Hochgurtel et al, PNAS, 2002, vol. 99, No. 6, pp. 3382-3387.
Greer et al, Journal of Medicinal Chemistry, 1994, vol. 37, No. 8, pp. 1035-1054.
Bramson et al, J. Med. Chem., 2001, vol. 44, pp. 4339-4358.
Blundell et al, Nature Reviews Drug Discovery, 2002, vol. 1, pp. 45-54.
Carr et al., Structure-based screening of low-affinity compounds, *Drug Discovery Today*, vol. 7, No. 9, May 1, 2002, pp. 522-527, XP002279162.
Eksterowicz et al., Coupling structure-based design with combinatorial chemistry: application of active site derived pharmacophores with informative library design, *Journal of Molecular Graphics & Modelling*, Jun. 2002, vol. 20, No. 6, pp. 469-477, XP002275868.
Lewis et al., Click chemistry *in situ*: acetylcholinesterase as a reaction vessel for the selective assembly of a femtomolar inhibitor from an array of building blocks, *Angewandte Chemie. International Edition, Verlag Chemie.*, vol. 41, No. 6, 2002, pp. 1053-1057, XP002967538.
Nguyen et al., Using an Enzyme's Active Site to Template Inhibitors, *Angewandte Chemie. International Edition, Verlag Chemie.*, vol. 40, No. 9, 2001, pp. 1774-1776, XP002275869.
Congreve et al., Detection of ligands from a dynamic combinatorial library by x-ray crystallography, *Angewandte Chemie (International Edition in English)*, Sep. 29, 2003, vol. 42, No. 37, Sep. 29, 2003, pp. 4479-4482, XP002275867.

* cited by examiner

SYNTHESIS AND SCREENING OF LIGANDS USING X-RAY CRYSTALLOGRAPHY

This application is the U.S. national phase of international application PCT/GB2003/005595 filed 22 Dec. 2003 which designated the U.S. and claims benefit of GB 0230172.9, filed 24 Dec. 2002, and claims priority to U.S. Provisional Application No. 60/435,349 filed 23 Dec. 2002, the entire contents of each of which are hereby incorporated by reference.

This invention relates to methods for synthesising compounds and identifying from those compounds ligands that bind target macromolecules using X-ray crystallography.

BACKGROUND

Determining the structure of proteins by X-ray crystallography is an elegant and reliable method and is the basis of structure-based ligand design in which small molecules are synthesized as potential ligands for the protein of interest. This is an intense area of research for the optimisation of ligands to drugs for therapeutically interesting proteins (see Babine, R. E. and Bender, S. L., *Chemical Reviews*, 97, 1359–1472 (1997) and Bohacek, R. S., et al., *Med. Res. Rev.*, 16, 3–50 (1996)).

One method of ligand screening is described in WO 99/45379, in which a library of shape-diverse compounds thought to be potential ligands are soaked or co-crystallised with a target protein, and then the resulting complex is analysed by X-ray crystallography to determine the nature of the ligand which has bound. The library of compounds which is used in the screening process generally comprises previously characterised compounds.

SUMMARY OF THE INVENTION

The above described method requires every potential ligand to be synthesized, purified and characterized before it can form part of a library for screening. If the potential ligands are simply purchased from commercial sources, their costs will typically be high due to the amount of work required to carry out these three steps. If, in the alternative, the compounds are to be synthesized 'in-house', then a great deal of time and effort will need to be expended on assembling the library of ligands for screening.

The present inventors have developed a method where a collection of compounds is synthesized and then screened without the need for any purification and/or characterisation steps.

Accordingly, the present invention provides a method for identifying a ligand of a target macromolecule comprising the steps of:
  a) soaking one or more crystals of the target macromolecule in a solution containing a collection of compounds generated in situ or separate from the crystal, where the solution has been prepared without the purification, and preferably without the characterisation, of the synthesized collection of compounds;
  b) obtaining an X-ray crystal diffraction pattern of the soaked macromolecule crystal; and
  c) using said X-ray crystal diffraction pattern to identify any compound bound to the macromolecule crystal, said compound being a ligand of the target macromolecule.

Any solvated crystal system in which the solvent and/or ligand molecules are able to infiltrate throughout the crystal via diffusion, and where the crystal system is compatible with X-ray diffraction data collection, is suitable for use in the invention.

Examples of appropriate macromolecules are polypeptides (proteins), ribose nucleic acids (RNAs, ribozymes etc), deoxy ribose nucleic acids (DNAs), and complexes of combinations of the three examples, e.g. ribosomes, or viruses (DNA and/or RNA-protein complexes).

A ligand is a molecule which can bind to a macromolecule. For a polypeptide chain (protein), this is anything that is not coded for by the DNA sequence of the protein. This covers the post-translational modification of proteins (e.g. covalent attachment of sugars, etc.), the covalent and non-covalent attachment of cofactors (e.g. Haem groups), the binding of other polypeptides or amino acids, the binding of small molecules (e.g. drugs, substrates, etc.) and the binding of DNA and RNA to proteins. For nucleic acids this is molecules either covalently, or non-covalently bound to DNA or RNA (e.g. ligands intercalated between bases).

In the present invention, the compounds can be synthesised by parallel synthesis, or (more conveniently) by combinatorial chemistry. Traditionally, combinatorial chemistry is used to generate small molecule inhibitors for screening against one or more biological targets. The synthesis of libraries of compounds has generally been aimed at producing either compounds as purified single entities or as high-quality mixtures of compounds using methodology that allows for deconvolution of the mixture, once it has been determined that an active compound is to be found in that mixture. Deconvolution requires the re-testing of each member compound of the active library. Thus either method requires the careful analysis and characterisation of the libraries to allow for interpretation of the data generated during biological screening against the target macromolecule. As mentioned above, the present invention does not require the purification and/or characterisation of the members of the synthesised library, as the identity of the ligand is determined by X-ray crystallography of the ligand-macromolecule complex.

The solution containing the collection of compounds can be prepared in two main ways, herein called 'in-situ' synthesis and 'just-in-time' synthesis.

'In-situ' synthesis involves synthesizing the collection of compounds in a solution which also contains the one or more crystals of the target macromolecule, and therefore requires the use of chemistries which can be carried out under conditions in which the macromolecule crystal will remain stable.

Accordingly, a first aspect of the present invention provides a method for identifying a ligand of a target macromolecule comprising the steps of:
  a) synthesizing a collection of compounds, which are suitable for screening against a target macromolecule, in a solution containing one or more crystals of the target macromolecule;
  b) obtaining an X-ray crystal diffraction pattern of the soaked macromolecule crystal; and
  c) using said X-ray crystal diffraction pattern to identify any compound bound to the macromolecule crystal, said compound being a ligand of the target macromolecule.

In this method, the synthesis of the collection of compounds will take place in a single reaction vessel, i.e. the vessel in which the solution containing one or more crystals of the target macromolecule is present.

'Just-in-time' synthesis involves synthesizing the collection of compounds remotely from the solution which contains the one or more crystals of the target protein, and then transferring the synthesized collection into the solution containing the one or more crystals of the target protein. No purification and/or characterisation of the synthesized collection is carried out. The synthesis may take place in a solvent which is not compatible with the macromolecule crystals, from which the collection of compounds must be separated in order to add them to the solution containing the macromolecule crystals.

Accordingly, a second aspect of the present invention provides a method for identifying a ligand of a target macromolecule comprising the steps of:
  a) synthesizing a collection of unpurified compounds suitable for screening against a target macromolecule
  b) adding the collection of compounds to a solution containing one or more crystals of the target macromolecule;
  c) obtaining an X-ray crystal diffraction pattern of the soaked macromolecule crystal; and
  d) using said X-ray crystal diffraction pattern to identify any compound bound to the macromolecule crystal, said compound being a ligand of the target macromolecule.

In this method, the synthesis of the collection of unpurified compounds may occur in one or more reaction vessels.

If step a) takes place in a solvent which is not compatible with the macromolecule crystals then after step a) the collection of compounds is separated from the solvent in which the compounds were synthesised.

Typically, such non-compatible solvents are organic and the step of separating the collection of compounds from this solvent is usually carried out by evaporating the solvent. This is then followed by re-dissolution of the collection of compounds in the solution containing the one or more macromolecule crystals.

Enzyme catalysis in organic solvents has attracted much interest in recent years (Mattos C. and Ringe D., *Curr Opin Struct Biol.*, 11(6), 761–4) and the use of enzymes in non-aqueous media has extended the field of biocatalysis (*ASGSB Bull.*, 4(2), 125–132 (1991)). Much work has been done to map out organic binding sites in crystals by soaking the crystals in organic solvents (English, A. C., et al., *Proteins*, 37, 628–640 (1999); Mattos C. and Ringe D., *Nauret Biotechnol.*, 14(5), 595–9 (1996)). In addition it has been shown that enzyme crystals can retain activity in organic solvents, both in the presence and absence of crosslinking agents (Ayala, M., et al., *Biochem. Biophys. Res. Comm.*, 295(4), 828–31 9 (2002)).

An alternative approach is to separate the non-compatible solvent from the solution containing the one or more macromolecule crystals by a permeable membrane, which allows transfer of the compounds in the collection from the non-compatible solvent to the solution containing the one or more macromolecule crystals. This approach requires a membrane which is porous enough to allow the diffusion of the synthesised compounds from the solvent in which they were synthesised to the solution containing the one or more macromolecules, whilst substantially preventing any diffusion of the solvents. Dialysis buttons provide one means by which this can occur, and are available, for example, from Hampton Research. Their use is described in 'Crystallisation of Nucleic Acids and Proteins, edited by Ducruix, A. and Giege, R., The Practical Approach Series, Oxford University Press, 1992.

The ligands identified by the methods of the present invention may be subsequently modified to alter their binding to the target macromolecule or to improve their usefulness as a pharmaceutical. Such modification is conventional in the art. Possible modifications include: substitution or removal of groups containing residues which interact with the target macromolecule, for example groups which interact with the amino acid side chain groups of a protein; the addition or removal of groups in order to decrease or increase the charge of a group in a compound; the replacement of a charge group with a group of the opposite charge; or the replacement of a hydrophobic group with a hydrophilic group or vice versa. Additionally, a group may be replaced with another retaining similar properties but that better occupies the cavity in the macromolecule increasing the surface of the ligand in contact with the macromolecule cavity. This may be achieved using the methodologies disclosed in this invention, or by conventional synthetic approaches typically utilised by those skilled in the art of medicinal chemistry. Many of these changes will improve the usefulness of a compounds as a pharmaceutical. It will be understood that these are only examples of the type of substitutions considered by medicinal chemists in the development of new pharmaceutical compounds and other modifications may be made, depending upon the nature of the starting compound and its activity.

Without wishing to be bound by theory, the detection of the ligand bound to the target macromolecule relies on the occupancy in the macromolecule crystals of one of the highest affinity ligands, this being driven by ligand-macromolecule interactions.

This method avoids disadvantages associated with biological screening methods in which the alteration of macromolecule activity by a potential ligand is assessed, as in that case compounds which bind weakly but non-specifically can alter macromolecule activity in a non-selective manner. Such non-selective inhibition produces false-positives, as the assay shows protein activity inhibition, but the compound would perform no useful function as a drug, as it would interfere with the activity of other proteins. Only compounds bound in a binding site will be detected by the present method. In particular, only compounds bound in a binding site with resolvable occupancy will be detected by the present method.

Binding sites are sites within a macromolecule, or on its surface, at which ligands can bind. Examples are the catalytic or active site of an enzyme (the site on an enzyme at which the amino acid residues involved in catalysing the enzymatic reaction are located), allosteric binding sites (ligand binding sites distinct from the catalytic site, but which can modulate enzymatic activity upon ligand binding), cofactor binding sites (sites involved in binding/co-ordinating cofactors e.g. metal ions), or substrate binding sites (the ligand binding sites on a protein at which the substrates for the enzymatic reaction bind). There are also sites of protein-protein interaction. If the macromolecule is a nucleic acid, then binding sites may be the bases of the nucleic acid, or spaces in their structures, e.g. the major or minor grooves in the helical DNA, interactions with phosphate, ribose or deoxy ribose groups or intercalated between the bases.

The present method also enables screening where the target macromolecule has more than one active site, as the data for each site can be analysed independently from the other sites to determine the compound bound in that site. In such cases, the information the method of the invention provides on the binding of two or more separate ligands to the target macromolecule can be used in the linked-fragment approach to drug design, in a similar manner to the method described by Greer, et al., *J. Med. Chem.*, 37(8), 1035–1054

(1994) for the synthesis of a thymidylate synthase inhibitor series. The basic concept behind linked-fragment approaches to drug design is to determine (computationally or experimentally) the binding location of plural ligands to a target molecule, and then to construct a molecular scaffold to connect the ligands together in such a way that their relative binding positions is preserved. The methods of synthesis and screening of the present invention may then be used to determine the best ligands from a library of such compounds, or individual compounds binding ability can be assessed using known methods.

Even if the present invention only provides information on the binding of ligands at a single binding site of a target macromolecule, a structure-based approach can be used to develop ligands which interact with further binding sites. Such a fragment growing approach is described in Blundell, T., et al., *Nature Reviews Drug Discovery*, vol. 11, 45–54 (2002).

It is preferred that the members of the collection of compounds are present at a concentration of at least 5 to 50 times, typically at least 10, their $K_i$ (depending case by case with the macromolecule used) so that the occupation of the binding site in the target macromolecule will not depend on the relative quantities of each compound in the collection.

In the case of competitive binding of a ligand to a macromolecule $K_i$ is defined as:

$$K_i = \frac{[M][L]}{[ML]}$$

where [M] is the concentration of the macromolecule, [L] is the concentration of free ligand, [ML] is the concentration of the ligand-macromolecule complex.

Where inhibitors are binding in an uncompetitive or non-competitive fashion the $K_i$ is defined as in Fundamentals of Enzyme Kinetics by A. Cornish-Bowden, Portland Press, 1995, ISBN 1 85579 0720, which is herein incorporated by reference.

It is preferred that the amount of each compound, being a member of the collection of compounds, present in the solution will be present at a concentration which is at least 5 or 10 times as much as the concentration of the target macromolecule in the reaction system, more preferably 100, 1 000 or even 10 000 times the concentration of the target macromolecule in the reaction system.

The binding of the ligands to the target macromolecule may be through non-covalent interactions or covalent bonding. If the target macromolecule is a protein, then covalent binding of the ligand to the protein may occur when the active site of the protein contains a catalytic residue such as in serine and cysteine proteases. If the target macromolecule is a nucleic acid, then certain classes of compounds are known to interact by covalent binding, e.g. pyrrolobenzodiazepines covalently bind to the exocyclic amino group of guanine.

In some embodiments of the present invention, it is preferred that the members of the collection of compounds do not bind covalently to the target macromolecule, but that they interact through non-covalent binding.

Further aspects of the invention relate to any novel compounds disclosed herein, their use as pharmaceuticals and their use in methods of therapy. In particular, further aspects of the invention include:

a) a ligand identified by the method of the present invention, or salts, solvates and chemically protected forms thereof;

b) a pharmaceutical composition comprising a ligand identified by the method of the present invention, or salts, solvates and chemically protected forms thereof, and a pharmaceutically acceptable carrier or diluent;

c) the use of a ligand identified by the method of the present invention, or salts, solvates and protected forms thereof, in a method of treatment of the human or animal body;

d) the use of a ligand identified by the method of the present invention, or salts, solvates and protected forms thereof, in the manufacture of a medicament for the treatment of a disease ameliorated by the binding of a ligand to the target macromolecule used in the method of the invention; and e) a method for the treatment of a disease ameliorated by the binding of a ligand to the target macromolecule used in the method of the invention comprising administering to a subject suffering from said disease a therapeutically-effective amount of a ligand identified by the method of the present invention, or salts and solvates.

Suitable carriers and diluents and information on pharmaceutical compositions can be found in standard pharmaceutical texts, for example, Handbook of Pharmaceutical Additives, 2nd Edition (eds. M. Ash and I. Ash), 2001 (Synapse Information Resources, Inc., Endicott, New York, USA); Remington's Pharmaceutical Sciences, 20th Edition, pub. Lippincott, Williams & Wilkins, 2000; and Handbook of Pharmaceutical Excipients, 2nd edition, 1994.

Further details of the invention will now be presented by way of explanation and example.

Although the discussion below focuses on the purification, crystal growth, X-ray crystallography and determination of ligand structure when the macromolecule is a protein, the techniques described are, in general, applicable to other macromolecules, such as nucleic acids and complexes, with appropriate modifications as known to the person skilled in the art.

Target Protein Purification.

A specific target protein can be isolated from animal, plant, or bacterial sources directly, or via recombinant methods. The generation of recombinant protein, using systems such as insect cells (e.g. *S. frugiperda*, or *Drosophila* cells), *E. coli*, yeast (*S. cerevisiae*, *S. pombe*, *P. Pastoris*, etc) or modified human cell lines, means that truncated, or otherwise genetically engineered, proteins can be generated. A protein crystallography project to obtain crystals normally necessitates access to a recombinant protein production system, but the method of the present invention may be performed with a single crystal, which may constitute, for example, between 0.1 and 100 µg.

It is generally accepted that the higher the degree of purity and homogeneity of a protein preparation the easier that it will be to grow protein crystals from the preparation. Protein purity reflects the number of protein species within a preparation. It also refers to the number, and nature, of any other non-protein species present (e.g. low molecular weight contaminants). An ideal protein preparation should contain solely one protein species, or one species of protein complex, in which all the protein molecules, or protein complexes, are identical in terms of their amino acid composition, mass etc. The purity of a protein preparation may be gauged via a variety of experimental techniques such as sodium dodecyl sulphate page (SDS-page) gels, mass spectrometry, antibody binding and detection (Western blotting), etc. Protein purities in excess of 90% are often deemed acceptable for crystallisation trials, but practitioners of the art of protein purification will generally try and strive for purities in excess of this arbitrary threshold, due to the perceived benefits of maximising protein purities.

Within a protein preparation, homogeneity can refer to the degree of uniformity observed for parameters such as the stoichiometry of proteins in a multiprotein complex, the mono-dispersity of the protein/complexes in solution, the oxidation, or protonation, state of amino-acid side chains, within proteins, the uniformity of post translational modifications (e.g. are all protein molecules within the population equivalently phosphorolated, glycosylated, or have any essential co-factors been uniformly and correctly incorporated) and the protein conformations that exist within a given population of protein molecules/complexes. The homogeneity of a protein preparation may be probed using a multitude of experimental methods some of which are: mass-spectrometry, Western blotting, SDS-page, analytical ultracentrifugation, size-exclusion chromatography, affinity chromatography, ion-exchange chromatography, hydrophobic interaction chromatography, surface plasmon resonance, activity assay, electron microscopy, dynamic light scattering (DLS), N-terminal sequencing, iso-electric focussing (IEF), proteolytic digest, fluorescence, circular dichroism (CD), native gel electrophoresis, bandshift assays, or nuclear magnetic resonance (NMR). Maximising the degree of homogeneity within a protein preparation is again deemed desirable, as maximising homogeneity is also believed to positively correlate with maximising crystallisability.

The Growth of Protein Crystals

Crystallisation of any species requires the formation of a supersaturated solution of the species in question and a nucleation event that is capable of initiating crystal growth. Post-nucleation the ambient conditions must be such that crystal growth can be sustained until the physical dimensions and properties of the crystals thus obtained are adequate for any subsequent experimental procedures required. Protein molecules typically only retain their structural integrity within an aqueous environment. Therefore protein crystals are normally grown in the aqueous phase. Protein crystals may grow if a nucleation event occurs in a pure and homogeneous protein solution that has been driven to a state of super-saturation.

Protein crystallisation is generally attempted using the vapour diffusion (sitting drop, hanging drop, sandwich drop, pH gradient etc), dialysis, batch, micro-batch, liquid-liquid diffusion, or in-gel-crystallisation methods. All these methodologies have been extensively described (Protein Crystallisation: Techniques, Strategies and Tips, Edited by T. M. Bergfors, IUL Biotechnology Series, 1999, Published by International University Line, La Jolla, Calif., ISBN: 0-9636817-5-3). All of the afore mentioned crystallisation processes function by generating a supersaturated protein solution, which promotes the spontaneous formation of crystallisation nuclei, and which is then subsequently able to sustain crystal growth.

There are diverse physico-chemical parameters that can influence whether or not a protein construct, or protein complex, will crystallise. Typically each protein crystallizes under a unique set of conditions, which cannot be predicted in advance. Simply driving the protein concentration to super-saturation, to bring it out of solution, will generally not work. The result would, in most cases, be an amorphous precipitate. Some parameters that may be varied are: the pH of solutions, the choice and concentration of buffer (if any) (e.g. Phosphate, MES, BIS-TRIS, TRIS, BES, PIPES, HEPES, MOPS, BICINE, CHES, CAPS etc), temperature, choice of crystallisation method (see above), volume of crystallisation, protein concentration, the addition of reducing agents (e.g. DTT, β-mercaptoethanol), detergents (e.g. decyl-β-D-maltoside, dodecyl-β-D-maltoside, ocytl-β-D-glucopyranoside, decanoyl-N-methylglucamide, Triton, octyltetraoxyethylene ether, etc.), alcohols (e.g. ethanol, isopropanol, methanol, 2-methyl-2,4-pentanediol (MPD)), salts (e.g. chlorides, acetates, sulphates, phosphates, bromides, iodides, fluorides, nitrates, bicarbonates, chlorates, chromates, citrates, tartrates, cacodylates, formates, hydroxides,. etc.), polyethylene glycols (PEGS), ethylene glycols, methoxy polyethylene glycols (MPEGS), heavy atoms and ions (e.g. iron, copper, zinc, cobalt, manganese, nickel, tungstates, vanadates, sodium, magnesium, potassium, lithium, calcium, aluminium, Xenon, etc.), or other additives such as dimethylsulfoxide (DMSO), denaturants (e.g. urea, guanadinium chloride, etc.), glycerol, sulfabetaines, jeffamines, AMPPNP, ATP, ADP, GTP, GDP peptides, tertiary-butanol, amino acids, azides, DNAs, RNAs, sugars, lipids, drugs, etc.

There are numerous crystallisation kits available (e.g. from Hampton Research), which attempt to broadly sample as many parameters in crystallization space as possible. In many cases these general screens help to identify a starting point for crystallisations in the form of crystalline precipitates and/or rough, or micro-, crystals. Typically these crystals are unsuitable for direct diffraction analysis and require further optimisation. Successful crystallization can be aided by knowledge of a protein's behaviour in terms of solubility, dependence on metal ions for correct folding or activity, interactions with other molecules and any other data that are available.

Systematically screening such a large number of parameters represents an extremely complex multi-dimensional search problem and is, as such, exceptionally difficult to perform in a systematic manner. Even with the advent of automated protein crystallisation it is often the case that crystallisation of a protein will require a very high degree of human input and the impact of intangible parameters such as serendipity, insight, and random error.

If preliminary crystals have been obtained it is often necessary to further modify the crystallisation conditions in an attempt to simultaneously maximise the internal order and physical dimensions of the crystals grown. Optimising these parameters is deemed beneficial for helping to maximise the data quality obtained in subsequent X-ray diffraction experiments. Identification of a set of initial crystallisation conditions reduces the potential parameter space that has to be explored, but crystal optimisation can still remain a time consuming and laborious process. Techniques such as macro- or micro-seeding may also aid crystal optimisation.

Details of some of the proteins crystallised, and information on some of the protein crystallisation conditions identified, are contained, for example, within the following internet databases:

http://wwwbmcd.nist.gov:8080/bmcd/bmcd.html (Gilland, G. L., et al., *Acta Crystallogr.*, D50, 408–413 (1994));

http://xray.bmc.uu.se/embo/structdb/links.html;

http://www.mpibp-frankfurt.mpg.de/michel/public/memprotstruct.html;

http://www.rcsb.org/pdb/ (Berman, H. M., et al., *Nucleic Acids Research*, 28, 235–242 (2000));

http://www.ebi.ac.uk/msd/ and have been described in the following publications:

Blundell, T., et al., "Protein Crystallography", Academic Press, New York (1976); McPherson, et al., "*Preparation and Analysis of Protein Crystals*" in "*Preparation and Analysis of Protein Crystals*", John Wiley & Sons, New York (1982); Carter, et al., "*Design of crystallization experiments and protocols.*", pages 47–71 in "Crystallization of Nucleic Acids and Proteins—A Practical Approach", (Ducruix, A. & Giege, R., eds) IRL Press, Oxford (1992); Ducruix, A., et al., "*Methods of crystallization.*", pages 73–98 in "Crystallization of Nucleic Acids and Proteins—A Practical Approach", (Ducruix, A. & Giege, R., eds) IRL Press, Oxford (1992); "Protein Crystallisation: techniques, stratagies, and tips." IUL Biotechnology Series (1999), ISBN 0-9636817-5-3.

Obtaining X-ray Diffraction Data from Soaked Protein Crystals

An X-ray diffraction experiment consists of exposing a protein crystal to a collimated, coherent, beam of X-rays and recording the resulting X-ray diffraction pattern. A diffraction pattern arises from the elastic scatter of X-rays off electrons within the planes of atoms within a protein crystal. The mathematics underlying X-ray diffraction may be represented in their simplest form by the Bragg equation:

$$n\lambda = 2d \sin \theta$$

where n is an integer, $\lambda$ is the wavelength of the incident X-rays, $\theta$ is the scattering angle of the X-rays off a given plane of atoms, and d is the Bragg spacing, or spacing between successive planes of atoms (Bragg planes). Thus as long as $\lambda$ corresponds to atomic scales (i.e. $\approx 1$ Å) then atomic scale features should be discernable within an electron density map calculated using the diffraction data. Typically it is considered that X-ray data are required to a Bragg spacing of $\leq 3$ Å, for a given X-ray wavelength, if the data from an X-ray diffraction experiment are to be of use in determining the atomic positions within a structure. During an experiment the various Bragg planes within a crystal will only satisfy the mathematical criteria necessary for diffraction at specific crystal orientations relative to the incident X-ray beam. So as to obtain diffraction data relating to as many Bragg planes as possible the crystal is rotated in the X-ray beam. Thus all possible plane orientations are explored. The angle through which a crystal must be rotated in order to obtain a complete set of data relating to a specific Bragg spacing is defined by the space group of the crystal and also the initial orientation of the crystal in the X-ray beam. The smallest Bragg spacing for which diffraction data are available is termed the resolution of the experiment. It is desirable to maximise the data completeness for an experiment. That is, data should ideally be 100% complete up to the resolution limit of the experiment.

Unfortunately the high energy of X-ray photons means that they cause damage to protein molecules. This is thought to be at least partially due to the generation of ions and free radicals within the crystals. Prolonged exposure of a protein containing crystal to an X-ray beam will thus result in a deterioration and decay of the proteins. This is typically manifested by a decline in the data resolution and quality. This problem may be partially circumvented by cryogenically freezing protein containing crystals in vitreous ice at 100K. Freezing of the crystal means that any ion, or free radical, species that are generated are unable to migrate through the crystal. Thus the longevity of the crystal in the X-ray beam is extended and the data quality and resolution typically improved relative to an unfrozen data collection. Normally protein containing crystals cannot be directly frozen in the solutions in which they grew (mother liquor). This is because direct freezing often leads to the formation of ice crystals within the mother liquor. These ice crystals can destroy the internal order within a protein crystal and thus abolish diffraction. The addition of a cryo-protectant to the protein's mother liquor can, however, lead to the formation of vitreous ice on freezing. This should not destroy the internal order of a protein crystal and thus retain diffraction from the crystal. Normally protein containing crystals must be transferred from their mother liquor into a specially formulated cryo-protectant solution prior to freezing. The exact composition of the cryo-protectant solution, the transfer protocol, and the freezing protocol must be uniquely determined for each crystal system and often for each experiment.

Determination of Ligand Structure

A mathematical operation termed a Fourier transform relates the diffraction pattern observed from a crystal and the molecular structure of the protein and ligand comprising the crystal (Blundell, T., et al., "Protein Crystallography", Academic Press, New York (1976); Drenth, "Principles of Protein X-ray Crystallography", Springer (1994)). A Fourier transform may be considered to be a summation of sine and cosine waves each with a defined amplitude and phase. Thus, in theory, it is possible to calculate the electron density associated with a protein and ligand structure by carrying out an inverse Fourier transform on the diffraction data. This requires amplitude and phase information to be extracted from the diffraction data. Amplitude information may be obtained by analysing the intensities of the spots within a diffraction pattern. The conventional methods for recording diffraction data do, however, mean that any "phase information" is lost. This phase information must be in some way recovered and the loss of this information represents the "crystallographic phase problem". The phase information necessary for carrying out the inverse Fourier transform can be obtained via a variety of methods.

If the structure of the unsoaked protein is already available, as would normally be the case, a set of theoretical amplitudes and phases may be calculated using the protein model and then the theoretical phases combined with the experimentally derived amplitudes. An electron density map may then be calculated and the protein and ligand structure observed. Electron density maps can be calculated using programs such as those contained in the CCP4 computing suite (Collaborative Computational Project 4, *Acta Crystallographica*, D50, 760–763 (1994)). For map visualization and model building programs such as "O" (Jones, et al., *Acta Crystallographica*, A47, 110–119 (1991)) or "QUANTA" (Jones, et al., (1991) and commercially available from Accelrys, San Diego, Calif.) can be used.

An alternative approach employs (i) X-ray crystallographic diffraction data from the complex of ligand and protein and (ii) a three-dimensional structure of the unsoaked protein, to generate a difference Fourier electron density map of the complex. The difference Fourier electron density map may then be analysed to identify the ligand.

Analysis of electron density maps may be aided by software, for example, AutoSolve® (Blundell, T., et al., *Nature Reviews Drug Discovery*, 11, 45–54 (2002)) or the ligand fitting module in QUANTA, XLIGAND (QUANTA: see above; X-LIGAND: Oldfield, T. J., *Acta Crystallogr D Biol Crystallogr.*, 57(5), 696–705 (2001)).

If there is no known structure of the protein then alternative methods for obtaining phases must be explored so as the resolve the structure of the unsoaked protein (Blundell, T., et al., "Protein Crystallography", Academic Press, New York (1976)). One method is multiple isomorphous replacement (MIR). This relies on soaking "heavy atom" (i.e. Platinum, Uranium, Mercury, etc) compounds into the crystals and observing how their incorporation into the crystals modifies the spot intensities observed in the diffraction pattern. An alternative method for obtaining phase information for a protein of unknown structure is to perform a multi-wavelength anomalous dispersion (MAD) experiment. This relies on the absorption of X-rays by electrons at certain characteristic X-ray wavelengths. Anomalous scattering by atoms within a protein will modify the diffraction pattern obtained from the protein crystal. Thus if a protein contains atoms which are capable of anomalous scattering a diffraction dataset (anomalous dataset) may be collected at an X-ray wavelength at which this anomalous scattering is maximal. The most usual way to introduce anomalous scatterers into a protein is to replace the sulphur containing methionine amino acid residues with selenium containing seleno-methionine residues. This is done by generating recombinant protein that is isolated from cells grown in controlled growth media that contains seleno-methionine (Doublie, S., *Methods in Enzymology,* 276, 523–530 (1997)). Selenium is capable of anomalously scattering X-rays and may thus be used for a MAD experiment. Another method generally available for the calculation of the phases necessary for the determination of an unknown protein structure is molecular replacement. This method relies upon the assumption that proteins with similar amino acid sequences (primary sequences) will have a similar fold and three-dimensional structure (tertiary structure). Examples of computer programs known in the art for performing molecular replacement are CNX (Brunger, A. T., et al., *Current Opinion in Structural Biology,* 8(5), 606–611 (1998) and also commercially available from Accelerys San Diego, Calif.) or AMORE (Navaza, J., *Acta Cryst.,* A50, 157–163 (1994)). The phase information obtained by one of these means, when combined with the experimentally obtained amplitudes from the native dataset, enables an electron density map of the unknown protein molecule to be calculated using the Fourier transform method.

If an electron density map has been calculated for a protein of unknown structure then the amino acids comprising the protein must be fitted into the electron density for the protein. This is normally done manually, although high resolution data may enable automatic model building. The process of model building and fitting the amino acids to the electron density can be both a time consuming and laborious process. Once the amino acids have been fitted to the electron density it is necessary to refine the structure. Refinement attempts to maximise the correlation between the experimentally calculated electron density and the electron density calculated from the protein model built (Blundell, T., et al., "Protein Crystallography", Academic Press, New York (1976) and "Methods in Enzymology", vols. 114 & 115, Wyckoff, H. W., et al., eds., Academic Press (1985)). Refinement also attempts to optimise the geometry and disposition of the atoms and amino acids within the user-constructed model of the protein structure. Sometimes manual re-building of the structure will be required to release the structure from local energetic minima. There are now several software packages available that enable an experimentalist to carry out refinement of a protein structure such as CNX (see above), or REFMAC (Murshudov, G. N., et al., *Acta Crystallographica,* D53, 240–255 (1997)). There are certain geometry and correlation diagnostics that are used to monitor the progress of a refinement. These diagnostic parameters are monitored and rebuilding/refinement continued until the experimenter is satisfied that the structure has been adequately refined.

The atomic coordinate data of the co-complexes formed from the methods of the invention can be routinely accessed using computer programs, for example, RASMOL (Sayle, et al., *TIBS,* 20, 374 (1995)), which is a publicly available computer software package, which allows access and analysis of atomic coordinate data for structure determination and/or rational drug design or AstexViewer™ which is contained in the CCP4 computing suite.

Information from X-ray Crystallography

The information obtained by the method according to the invention can be used to provide much more information that the identity of the ligand which has bound. As the information on the ligand results from fitting to the electron density measured in the protein active site, this can allow the mode of binding and interactions to be ascertained, which can be useful in further elaboration and optimisation of the ligand.

The Collections of Compounds

The collection of compounds for use in the present invention are produced by one or more synthetic processes designed to connect two or more sets of monomers together. Monomers are molecules which share a common reactivity that makes them capable of combining with another complementary monomer to form a larger compound. Each set of monomers will contain at least one monomer and preferably no more than 100 monomers, such that between about 5 and about 1000 compounds are in each collection of compounds. It is preferred that all the compounds in a collection comprise a common functional group (sometimes referred to as a 'templating moiety') which is produced by the reaction of two or more complimentary functional groups present on the monomer sets used in the synthetic process. In one preferred embodiment each compound in a collection is related to other members of the collection by virtue of being synthesised from at least one common monomer unit. By having common features or trends in the structures of the compounds in the collection, it makes it possible to identify which moieties in the compounds (derived from individual monomer units) bind best to the target protein, even if the independent monomer itself does not have any detectable binding. This is achieved by observing the preference for binding that the macromolecule exhibits for compounds from the collection.

It is further preferred that the collection of compounds will have shape features that differ sufficiently to allow at least one set of monomers used in their production to be distinguished from each other. This then allows determination of the chemical structure of the bound ligand, or to at least determine part of its structure. If only part of its structure can be determined, re-synthesis of some of the members of the collection of compound that contain this partial structure will be necessary and these compounds are soaked into the crystal as singlet experiments so that the chemical structure of the bound ligand or ligands can be determined. This type of re-synthesis approach is termed a chemical deconvolution and is well known to practitioners of combinatorial or parallel synthesis to identify the biologically active member from a mixture of synthesised compounds.

'In-situ' Synthesis

As mentioned above, protein crystals are sensitive to the media in which they are grown and kept, and therefore the methods chosen for 'in-situ' synthesis, i.e. synthesis of the collection of compounds in the presence of the target protein crystals, have to be chosen such that they can occur under conditions which will not destroy the target protein crystal. If some degradation of the crystals occur, this should not be to such an extent that the X-ray diffraction results are not of sufficient quality to allow for identification of the ligand (see above).

Typically reactions are those which can be carried out in a purely aqueous media at around room temperature (4 to 30° C.), and at a pH of 4 to 10.

Examples of these chemistries, which apply to both methods of combinatorial synthesis and parallel synthesis, include: Acetal or Ketal formation; Addition reactions; Aldol condensations and related condensation reactions; Allylations; Cycloaddition reactions; Disulfide formation; Hydrazone formation; Mannich reactions; Michael reactions and related Conjugate Addition reactions; Palladium mediated reactions; Reductive alkylation; Substitution reactions; and Three or Four Component Reactions.

The following reactions can be carried out using synthetic procedures described in general organic chemistry texts such as March's Advanced Organic Chemistry (Smith, M. B. and March, J., 5th edition, Wiley-Interscience, New York, 2001) or references given therein. Some synthetic reactions carried out in aqueous conditions have recently been reviewed by Ulf Lindstroem, see "Stereoselective Organic Reactions in Water", *Chemical Reviews*, 102(8), 2751–2771 (2002). The practice of combinatorial chemistry is described in references cited in publications by Roland Dolle (*Journal of Combinatorial Chemistry*, 4(5), 369–418 (2002); *Journal of Combinatorial Chemistry*, 3(6), 477–517 (2001); *Journal of Combinatorial Chemistry*, 2(5), 383–433 (2000); *Molecular Diversity*, 4(4), 233–256 (2000); *Journal of Combinatorial Chemistry*, 1(4), 235–282 (1999); *Molecular Diversity*, 3(4), 199–233 (1998)).

These reactions take place between appropriate sets of ligand precursor molecules ('monomers'), which are represented schematically below, with M representing a substituent group that is varied in each monomer set (e.g. $M_1$, $M_2$, $M_3$, etc.). Each reacting set of monomers can have as few as a single member, up to, for example, 40 members, although a maximum of about 20 members would be more usual. In some embodiments of the invention it is preferred that each set of reacting monomers comprises at least two monomers. A typical size for the resulting collection of compounds would be between 5 and 1000, preferably between 5 and 100, with a range 10 or 20 to 50 or 70 being preferred.

In the following examples, R represents a substituent or H on a monomer.

Acetal or Ketal Formation

Addition of alcohols or a diol to an aldehyde or ketone, catalysed by acid. The reactions are fully reversible leading to thermodynamic products.

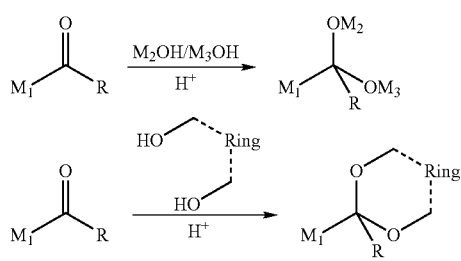

Addition Reactions

For example, addition to an epoxide under acidic conditions, or addition of alcohols to enol ethers.

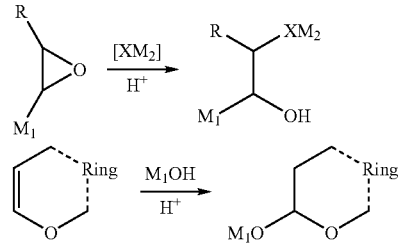

X=O, S, N or P, and where the ring may be optionally substituted on any available position.

Aldol Condensations and Related Condensation Reactions

For examples, see Kobayashi, S. and Manabe, K., *Accounts of Chemical Research*, 35(4), 209–217 (2002).

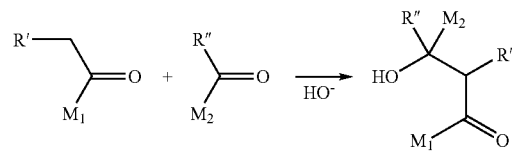

Related condensation reactions are the Knoevenagel reaction, the Peterson reaction, the Perkin reaction, the Darzen's reaction, Tollens' reaction, the Wittig reaction and the Thorpe reaction. Careful selection of the monomers is required in order for these reactions to proceed under aqueous conditions.

Allylations

For examples, see Kobayashi, S. and Hachiya, I., *Yuki Gosei Kagaku Kyokaishi*, 53(5), 370–80 (1995).

Cycloaddition Reactions

For example, the Diels-Alder reaction, see Fringuelli, F., et al., *European Journal of organic Chemistry*, 3, 439–455 (2001).

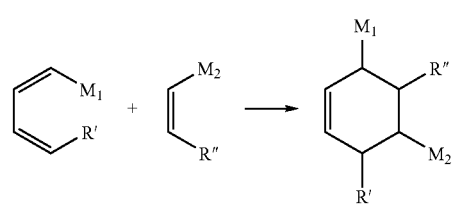

Many variations exist of the above formula, including where heteroatoms are incorporated (e.g. aza-Diels-Alder reactions) Cycloadditions to form 5 membered ring systems are also very general and an illustrative example is the cycloaddition of nitrile oxides with alkynes to form oxazoles which occurs at room temperature under very mild conditions.

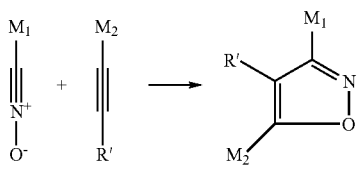

An example of a cycloaddition reaction that is water-tolerant is the "click chemistry" described by Sharpless in Lewis, et al., *Angew. Chem. Int. Ed.*, 41(6), 1053–1057 (2002). In this an azide and an acetylene undergo a Huisgen 1,3-dipolar cycloaddition to give 1,2,3-triazoles.

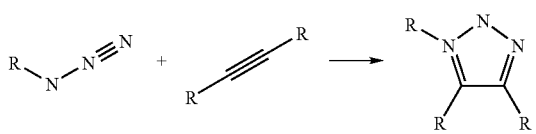

Disulfide Formation

Occurs reversibly under very mild conditions.

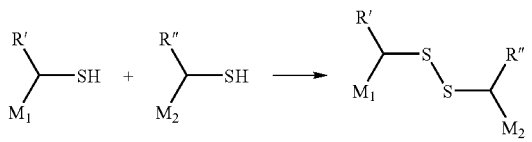

Hydrazone Formation

Occurs reversibly under very mild conditions.

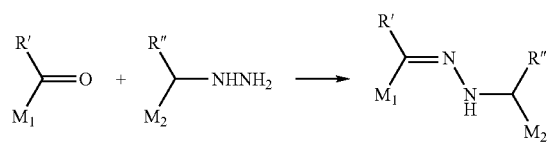

Mannich Reactions

For examples, see Akiyama, T., et al., *Advanced Synthesis & Catalysis*, 344(3+4), 338–347 (2002).

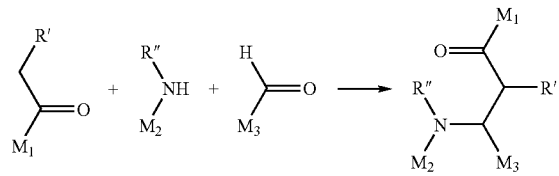

Michael Reactions and Related Conjugate Addition Reactions

Addition of nucleophiles to α,β-unsaturated carbonyl compounds is another example of addition reactions suitable for use in the invention.

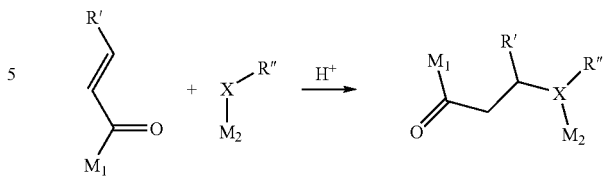

The carbonyl can also be replaced by other electron withdrawing groups, such as nitro groups, see Da Silva, F. and Jones, J., *Journal of the Brazilian Chemical Society*, 12(2), 135–137 (2001).

A related transformation is the Baylis Hillman reaction, see Yu, C., et al., *Journal of Organic Chemistry*, 66(16), 5413–5418 (2001).

Palladium Mediated Reactions

Many palladium mediated reactions can be carried out in aqueous media, e.g. Heck, Sonogashira, Tsuji-Trost, Suzuki, Stille, see Pierre Genet, J. and Savignac, M., *Journal of Organometallic Chemistry*, 576(1–2), 305–317 (1999). A representative illustration is the Suzuki cross coupling reaction:

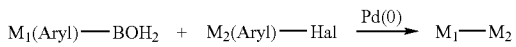

Reductive Alkylation

Occurs under very mild conditions. An example carried out in the presence of a protein is Hochguertel, M., et al., *Proceedings of the National Academy of Sciences of the United States of America*, 99(6), 3382–3387 (2002).

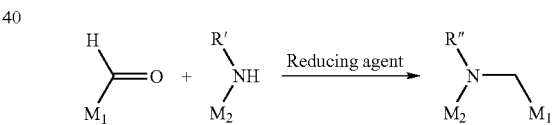

Substitution Reactions

Many useful substitution reactions occur under aqueous conditions, e.g. nucleophilic displacement (with alcohols, amines, thiols, carboxylic acids, enolates, hydrazines, dithianes etc) of alkyl halides, tosylates, mesylates and azides; ester, amide and urea formation by displacement of an activated ester or carbonate or carbamate; and aromatic nucleophilic substitution of electron deficient aromatic compounds with amines, alcohols, thiols etc.

An example of alkylation chemistry in the presence of a protein is Nguyen, R. and Huc, I., *Angew. Chem. Int. Ed.*, 40(9), 1774–6 (2001)

A generic scheme is as follows:

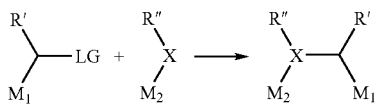

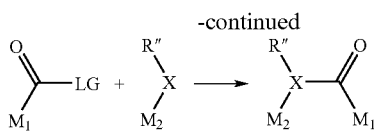

Where LG is a leaving group, and X is a nucleophilic heteroatom or carbon anion.

Three or Four Component Reactions

A number of multicomponent reactions proceed under mild mixed aqueous conditions and are suitable for combinatorial library design for the purposes of this invention. One example is the Ugi condensation (see Domling, A., *Current Opinion in Chemical Biology*, 6(3), 306–313 (2002); Ugi, I., et al., *Combinatorial Chemistry*, 125–165 (1999)):

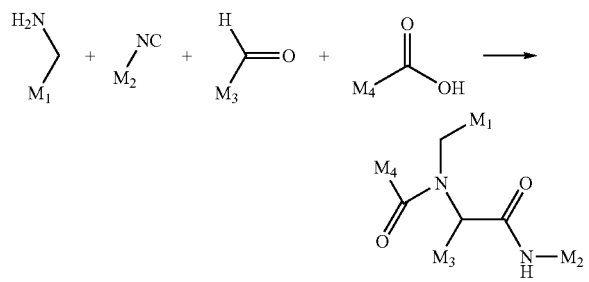

Also encompassed in the scope of the invention is design of combinatorial reactions in which more than one functional group can be present on any given monomer so that multimeric ligands can be assembled. In this way two or more monomers can be assembled by two or more functional group interconversions using chemistry illustrated above or other chemistry possible under mild aqueous conditions. For example, schematically:

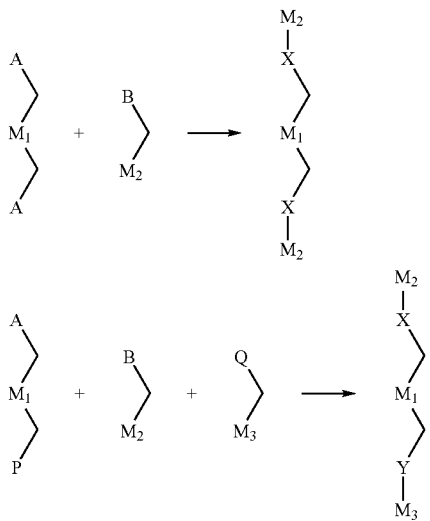

in which the monomer sets containing groups $M_1$ and $M_2$ react together through one chemistry (A+B=X) to give trimeric products containing the groups $M_1$ and $M_2$, and monomer sets containing $M_1$, $M_2$ and $M_3$ react together through two chemistries (A+B=X and P+Q=Y) to give trimeric products containing the groups Ml and $M_2$ and $M_3$.

Other factors which need to be considered in designing suitable combinatorial library conditions under aqueous conditions are as follows:

Solubility in water of the reacting monomers may be limiting to the efficiency of the transformations Catalysis—Bronsted and Lewis acid catalysis and other catalysts may be used to allow a transformation to proceed in an aqueous environment [For example Lindstroem, U., *Chemical Reviews*, 102(8), 2751–2771 (2002).]

Micelles—the use of micellar catalysts to enable the use of water as a solvent [For examples see Lindstroem, U. (2002)]

Cosolvents—the use of cosolvents to enable the use of water as a solvent including, but not limited to, DMSO, polyethylene glycols, ethylene glycols, methanol, ethanol, isopropanol, acetone and acetonitile. These cosolvents should be compatible with the protein crystal and may typically be used in an amount of up to 20% of the solvent system, which is preferred, although an amount of up to 40% or higher may be possible.

Solubilisers—the use of solubilising agents to enable the use of water as a solvent in reactions of organic compounds. [For examples see Lindstroem, U., (2002)]

Surfactants—the use of surfactants to enable the use of water as a solvent in reactions of organic compounds. [For examples see Lindstroem, U., (2002)] These surfactants should be compatible with the protein crystal.

The above described combinatorial library synthesis and procedures can similarly be adapted for mixed aqueous solvent conditions.

In some embodiments of the present invention, it is preferred that the monomers cannot substantially bind to the target protein, but that only the collection of compounds formed include compounds that show affinity for the target protein. Preferably the ratio of the $K_i$ of the strongest binding ligand formed to the $K_i$ of the strongest binding monomer is at least 10 to 1, more preferably 100, 1000 or even 10000 to 1.

In a preferred case, it is possible that the presence of the protein crystal in the solution in which the combinatorial chemistry takes place will exert an influence on the reactions occurring. If the reactions are reversible, then without wishing to be bound by theory, this would allow generation of thermodynamic products having the advantage of allowing for the 'local enrichment' of products at the protein surface leading to formation of the most potent ligand possible in the library. The principles of this effect are described by Huc, I. and Nguyen, R., *Combinatorial Chemistry and High Throughput Screening*, 109–130 (2001). If the reactions are irreversible, then without wishing to be bound by theory, this would allow generation of kinetic products having the advantage of 'local templating' of products at the protein surface leading to formation of the most potent ligand possible in the library. The principles of this effect are described by Nguyen, R. and Huc, I., *Angew. Chem. Int. Ed.*, 40(9), 1774–6 (2001) and in 'click chemistry' e.g. Lewis, W., et al., *Angew. Chem. Int. Ed.*, 41(6), 1053–1057 (2002).

'Just-in-time' Synthesis

As 'just-in-time' synthesis is not carried out in the presence of the protein crystals, there is less restriction on the types of chemistries that can be used to generate the collections of compounds for screening. However, in selecting appropriate starting materials and reaction conditions, it is preferred that the reactions do not result in a large number of by-products that could interfere with the screening process, and so reactions that do not require extraneous reagents are preferred.

The reactions discussed above in relation to the 'in-situ' synthesis would be particularly suitable, but other reactions could be considered, for example those using methodology in which the reagents that catalyse or drive the synthetic conversions are bound onto a solid phase medium and therefore removed from the solution by filtration. These chemistries, suitable for use with this invention, are described by Ley, S. V., et al., *Perkin* 1, 23, 3815–4195 (2000) and references cited therein.

Such reactions can be carried out using synthetic procedures described in general organic chemistry texts such as March's Advanced Organic Chemistry (Smith, M. B. and March, J., 5$^{th}$ edition, Wiley-Interscience, New York, 2001) or references given therein, and reference is also made to the texts on the practice of combinatorial chemistry given above.

As in 'in-situ' synthesis, the reactions take place between appropriate sets of ligand precursor molecules ('monomers'), in which at least one substituent group is varied, to result in sets of monomers. Each reacting set of monomers can have as few as a single member, up to, for example, 40 members, although a maximum of about 20 members would be more usual. In some embodiments of the invention it is preferred that each set of reacting monomers comprises at least two monomers. A typical size for the resulting collection of compounds would be between 5 and 1000, preferably between 5 and 100, with a range 10 or 20 to 50 or 70 being preferred.

The usual purification and characterisation steps which are used in the practice of combinatorial or parallel synthesis are not required in methods according to the present invention. These steps are viewed as essential in the conventional practice of these synthesis methods in order to produce compounds suitable for testing in a biological assay, as described in many of the references cited herein. Purification does not involve physical separation techniques such as solvent evaporation or removal of insolubles, e.g. by sedimentation, centrifugation or filtration. Conventional purification methods include aqueous extraction, trituration, chromatography such as flash column chromatography or HPLC purification, crystallisation and distillation, although certain characterisation methods can also be used in purification. Characterisation may be carried out in a number of ways, including using LCMS, MS and NMR analysis.

In a particularly preferred embodiment of the invention, the chemistry used for the 'just-in-time' synthesis is carried out in a solvent suitable as a co-solvent for aqueous solutions of protein crystals. Such solvents include DMSO, NMP and alcohols such as methanol and ethanol (for more details, see discussion of cosolvents in 'in-situ' synthesis). In this way, after incubation of the reaction for a suitable period of time, aliquots can be taken of the solution and added directly to the protein crystal containing solution, without the need for any purification or characterisation steps.

EXAMPLE

The protein chosen as the target macromolecule was cyclin-dependent kinase 2 (CDK2). This target has been the subject of intense study with the aim of developing inhibitors for the treatment of a number of human cancers, and has been crystallized with a number of inhibitors bound in the ATP-binding groove (De Azevedo, W. F., et al., *Eur. J. Biochem.*, 243, 518–526 (1997); Hoessel, R., et al., *Nat. Cell Biol.*, 1, 60–67 (1999))

The collection of compounds chosen for synthesis were based on the oxindole template, being a class of inhibitors already disclosed for CDK2 (Bramson, H. N., et al., *J. Med Chem.*, 44, 4339–4358 (2001)). These ligands (AB; Scheme 1) present substituents in adjacent lipophilic binding pockets within the ATP binding groove and can be disconnected to monomers of approximately equal size and complexity (hydrazines A and isatins B; Scheme 1).

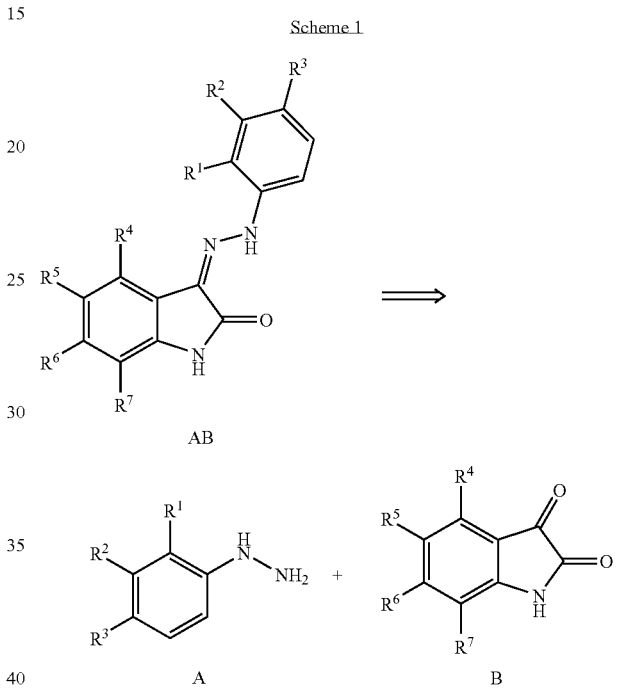

Scheme 1

A range of hydrazines (A1 to A6; Table 1) and isatins (B1 to B5; Table 1) were chosen, so that the collection of oxindoles formed would present a range of functional groups to the ATP binding site.

TABLE 1

| Hydrazines | | Isatins | |
|---|---|---|---|
| A1 |  | B1 |  |
| A2 |  | B2 |  |

TABLE 1-continued

| Hydrazines | Isatins |
|---|---|

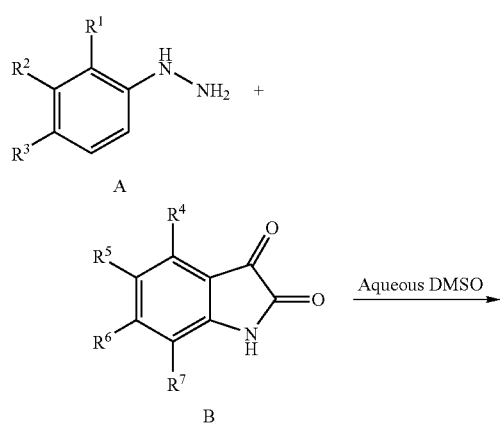

The synthesis of the collection of ligands was then demonstrated to proceed under aqueous conditions in the presence of 20% of the co-solvent dimethylsulfoxide (DMSO), according to scheme 2:

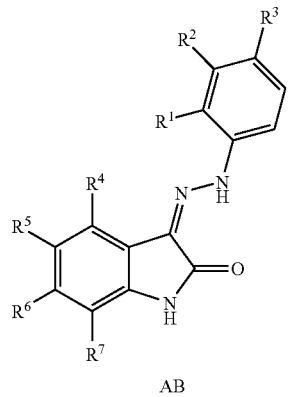

Analysis by mass spectrometry of the 30 reactions in the array indicated that all reactions successfully formed the expected products over a 24–72 hour period and the efficiency of the individual reactions was assessed by LC/MS analysis (Table 2). In most cases, under these reaction conditions, the products slowly precipitated from the reaction solution over time. It is clear from the qualitative data presented in Table 2 that monomer A6 did not give high conversions or high purity in the reactions and that some other individual reactions were also poor, however, the variability in absolute amount of products formed between individual reactions would be expected to be no more than 10-fold from these results.

TABLE 2

(% purity by peak area of product by LC/MS)

| A × B | A1 | A2 $R^1$ = Cl | A3 $R^2$ = Cl | A4 $R^3$ = Cl | A5 $R^3$ = $SO_2NH_2$ | A6 $R^1$ = Cl; $R^3$ = $SO_2Me$ |
|---|---|---|---|---|---|---|
| B1 $R^5$ = $NO_2$ | 10–25 | 60–95 | 60–95 | 30–50 | 60–95 | 30–50 |
| B2 $R^5$ = Cl | 60–95 | 60–95 | 60–95 | 60–95 | 60–95 | 30–50 |
| B3 $R^5$ = $SO_3H$ | 10–25 | 60–95 | 30–50 | 10–25 | 60–95 | 30–50 |
| B4 $R^7$ = $CF_3$ | 30–50 | 60–95 | 60–95 | 60–95 | 60–95 | 30–50 |
| B5 $R^5$ = $OCF_3$ | 30–50 | 60–95 | 60–95 | 60–95 | 60–95 | 10–25 |

R groups = H unless indicated otherwise.

Monomer studies to investigate kinetic competition of the monomers indicated that the products formed non-stoichiometric mixtures since it would be expected that the hydrazines and isatins would have varying reactivities. LC/MS analysis of competition experiments (using Photodioide Array Detector scanning from 200–400 nm wavelengths) indicated that mixtures of the hydrazines reacted with a 10-fold deficit of each isatin gave less than a 5-fold excess of any individual product over any other and typically less than 3-fold excess. These data again indicated that monomer A6 tended to be disfavored but again a measurable amount of product resulting from reaction of this monomer with each isatin was detected (5–10% of the mixture).

These results show that during ligand synthesis in the presence of the protein all of the reaction products were capable of being formed at a useful concentration. Additionally, under these conditions, thermodynamic products would be expected to predominate because the reactions are fully reversible.

Analysis of the reactions, e.g. by LC-MS and isolation of the compounds is not required for the method of the invention, but having now established reaction conditions suitable for use in the X-ray screening method disclosed in this invention, it is now possible to change the substitution patterns present in the monomer sets A and B (i.e. $R^1$—$R^7$) and to carry out in situ synthesis of further libraries of compounds, not described herein, in the presence of CDK2 crystals.

Crystals of full length (residues 1–298), human, cdk2 were grown. For soaking purposes crystals were transferred into a solution that maintained the ionic strength and precipitant concentrations of the original crystal mother liquor, but also contained 20% DMSO and the hydrazine and isatin reactive species (see Table 3). In all cases the total hydrazine concentration was in 10-fold excess over the isatin concentration.

The present invention also includes the use of the aforementioned methods for the generation of CDK2 ligands.

Experimental Methods

Crystals of full length (amino acids 1–298) human cyclin dependent kinase 2 (cdk2) were grown under the conditions detailed in (1) Lawrie, et al., Nat. Str. Biol., 4, 796–800 (1997) and (2) Rosenblatt, J., et al., J. Mol. Biol., 230, 1317–1319 (1993). Crystals grown using (1) were obtained using the hanging drop, vapour diffusion method, at 4° C., or 18° C. 1 µl of 10 mg/ml cdk2 in 10 mM Hepes/NaOH pH 7.4, 15 mM NaCl, was mixed with 1 µl of reservoir solution. The reservoir solutions (1 ml total volume) contained (25–55) mM ammonium acetate, (10–17.5)% polyethylene glycol (PEG)(average molecular weight 3350) and 100 mM HEPES/NaOH pH 7.4. Crystals grown using (2) were also produced by the hanging drop, vapour diffusion, method at 4° C. 4 µl of 10 mg/ml cdk2 in 10 mM HEPES/NaOH pH7.4 were suspended over a 1 ml reservoir solution containing (200–800) mM HEPES/NaOH pH 7.4.

For soaking purposes crystals grown using (1) were transferred into microbridges containing 20 µl of soak solution. Soak solutions were prepared such that the ammonium acetate, PEG and HEPES/NaOH pH 7.4 concentrations were identical to the drop from which a given crystal was harvested. The soak solutions further contained 20% DMSO and the hydrazine and isatin species that were to be reacted. Hydrazine and isatin concentrations in the ranges (5–20) mM (total organic) and (0.5–2) mM (total organic) respectively were used. Total organic refers to the fact that in a soak solution containing multiple isatins and hydrazines the combined concentration of all the hydrazines would be (5–20) mM and the combined concentration of all the isatins would be (0.5–2 mM). All hydrazines were present in equimolar concentrations and all isatins were present in equimolar concentrations. That is; if a soak solution contained two isatins and four hydrazines with total organic hydrazine and isatin concentrations of 10 mM and 1 mM respectively each of the isatins would be present at a concentration of 0.5 mM and each of the hydrazines at a concentration of 2.5 mM. Soak solutions typically contained permutations of (1–5) isatins and/or (1–6) hydrazines (see Table 1.). The generic formula for the products formed by permuting the reactants is given in Scheme 2 (see also Table 2.). The exact nature of the products formed is detailed in Table 2. Crystals were soaked for 3–5 days at 18° C.

Crystals were frozen by momentarily dipping them into a cryo-protectant solution and then snap cooling them in liquid nitrogen. The cryo-protectant solutions contained (17.5–22.5)% glycerol and ammonium acetate, PEG and HEPES/NaOH pH 7.4 concentrations that were identical to the drops from which the crystals were originally harvested.

Crystals grown using (2) were soaked, and frozen identically to those grown using (1), except that rather than maintaining ammonium acetate, PEG and HEPES/NaOH pH 7.4 concentrations only the HEPES/NaOH pH 7.4 concentration was maintained.

X-ray diffraction data were collected from soaked crystals, cooled to 100K, on a Rigaku copper rotating anode source using Rigaku/MSC Jupiter CCD, or Raxis IV++ image plate, detectors. The data were integrated, reduced and scaled using either the D*TREK suite (Pflugrath, J. W., Acta Crystallographica, D55, 1718–1725 (1999)), or MOSFLM (Leslie, A. G. W. In Joint CCP4 and EESF-EACMB Newsletter on Protein Crystallography, vol. 26, Warrington, Daresbury Laboratory (1992)), SCALA and the CCP4 suite of programs (CCP4:see above). An apo-cdk2 structure (DeBondt, H. L., et al., Nature, 363, 595–602 (1993)) was used as a starting point for structure refinements. The structures were initially segmented into 25 amino acid sections and rigid-body refined in CNX (see above). The structures were then subjected to iterative cycles of positional and isotropic B-factor refinement in CNX, followed by manual rebuilding using the graphics program "O" (see above) and automated ligand fitting using AUTOSOLVE®. Final water fitting was performed using in-house software. Details of representative X-ray data are given in Table 3.

TABLE 3

Representative X-ray results and experimental conditions

| Components in soaking solution | A5 + B2 | A5 + B3 | A5 + B5 | A5 + B1 | B2 + (A1, A2, A3, A4) | B2 + (A1, A2, A3, A4, A5, A6) | (B1, B2, B3, B4, B5) + (A1, A2, A3, A4, A5, A6) |
|---|---|---|---|---|---|---|---|
| Space group | $P2_12_12_1$ | $P2_12_12_1$ | $P2_12_12_1$ | $P2_12_12_1$ | $P2_12_12_1$ | $P2_12_12_1$ | $P2_12_12_1$ |
| a (Å) | 53.68 | 53.69 | 53.50 | 53.73 | 53.53 | 53.62 | 53.69 |
| b (Å) | 71.94 | 71.94 | 71.41 | 72.11 | 71.48 | 71.83 | 72.41 |
| c (Å) | 71.90 | 72.25 | 72.12 | 72.36 | 72.22 | 71.89 | 72.10 |
| Maximal resolution | 2.20 | 2.25 | 2.65 | 2.70 | 2.20 | 2.20 | 2.80 |
| Observations | 36740 | 41480 | 22249 | 23195 | 36709 | 35997 | 22680 |
| Unique reflections | 14265 | 13583 | 8277 | 8470 | 14171 | 14250 | 6991 |

TABLE 3-continued

Representative X-ray results and experimental conditions

| Components in soaking solution | A5 + B2 | A5 + B3 | A5 + B5 | A5 + B1 | B2 + (A1, A2, A3, A4) | B2 + (A1, A2, A3, A4, A5, A6) | (B1, B2, B3, B4, B5) + (A1, A2, A3, A4, A5, A6) |
|---|---|---|---|---|---|---|---|
| Completeness (%) | 97.2 | 98.5 | 98.2 | 98.6 | 92.7 | 89.1 | 96.9 |
| $R_{merge}$ | 0.088 | 0.153 | 0.122 | 0.143 | 0.057 | 0.035 | 0.127 |
| Mean I/σI | 4.3 | 4.1 | 3.8 | 3.7 | 6.2 | 8.6 | 4.8 |
| Highest resolution bin (Å) | 2.28–2.2 | 2.33–2.25 | 2.74–2.65 | 2.74–2.65 | 2.28–2.2 | 2.28–2.2 | 2.95–2.8 |
| Completeness (%) | 88.5 | 97.8 | 99.5 | 100 | 86.8 | 85.2 | 98.0 |
| $R_{merge}^{1}$ | 0.28 | 0.284 | 0.332 | 0.344 | 0.187 | 0.134 | 0.258 |
| Mean I/σI | 2.0 | 2.4 | 2.0 | 2.1 | 2.3 | 3.0 | 2.8 |
| Refinement | | | | | | | |
| Protein atoms | 2279 | 2279 | 2279 | 2279 | 2279 | 2279 | 2279 |
| Other atoms | | | | | | | |
| Inhibitor | 23 | 26 | 27 | 25 | 0 | 23 | 23 |
| Water | 139 | 129 | 57 | 39 | 245 | 229 | 67 |
| Resolution range (Å) | 35–2.2 | 35–2.25 | 35–2.65 | 35–2.7 | 35–2.2 | 35–2.2 | 35–2.8 |
| $R_{conv}$ (%)$^{2}$ | 25.9 | 24.7 | 23.7 | 24.3 | 25.6 | 24.6 | 21.1 |
| $R_{free}$ (%)$^{3}$ | 30.6 | 28.9 | 29.0 | 28.1 | 27.2 | 25.5 | 24.9 |
| Mean B-factor (Å$^{2}$) | | | | | | | |
| Protein | 37.0 | 38.1 | 42.2 | 49.0 | 26.1 | 30.8 | 30.6 |
| Ligand | 31.2 | 37.3 | 47.0 | 59.7 | NA | 24.3 | 25.5 |
| Solvent | 47.2 | 42.8 | 35.5 | 50.4 | 34.2 | 41.5 | 34.8 |
| Soaks | | | | | | | |
| Isatin conc (mM) | 2$^{6}$ | 0.5$^{6}$ | 0.5$^{6}$ | 1$^{6}$ | 1 | 1 | 1 (total organic$^{4}$) |
| Hydrazine conc (mM) | 20 | 5 | 5 | 10 | 10 (total organic$^{4}$) | 10 (total organic$^{4}$) | 10 (total organic$^{4}$) |
| Soak time (days) | 5 | 3 | 3 | 3 | 3 | 3 | 3 |
| Product present | YES$^{5}$ | YES$^{5}$ | YES$^{5}$ | YES$^{5}$ | NO$^{5}$ | YES$^{5}$ | YES$^{5}$ |

$^{1}R_{merge} = \Sigma_h \Sigma_j |I_{h,j} - I_h|/\Sigma_h \Sigma_j |I_{h,j}|$, where $I_{h,j}$ is the j$^{th}$ observation of reflection h.
$^{2}R_{conv} = \Sigma_h ||F_o| - |F_c||/\Sigma_h |F_o|$, where $F_o$ and $F_c$ are the observed and calculated structure factor amplitudes respectively for the reflection h.
$^{3}R_{free}$ is equivalent to $R_{conv}$, but for a 5% subset of the reflections not used for refinement.
$^{4}$total organic refers to the total combined isatin, or hydrazine concentration in the soak. Each component being present at a concentration equal to the total organic concentration divided by the number of isatin, or hydrazine, components in the mix.
$^{5}$Control experiments with crystals soaked for (3–5) days in cocktails containing either B2(20 mM), (B1, B2, B3, B4, B5) (1 mM total organic$^{4}$), or (A1, A2, A3, A4, A5, A6) (1 mM total organic) did not reveal any interpretable ligand density. Crystals soaked in a 10 mM cocktail of (A1, A2, A3, A4, A5, A6) were repeatedly destroyed.
$^{6}$In certain instances it was found that crystals subjected to soaks that contained only one hydrazine and one isatin sustained increased damage as compared to those soaked in multi-component isatin-hydrazine cocktails. Isatin and hydrazine concentrations were iteratively reduced until soaking crystals could be stabilised, and crystal damage diminished. Precipitation, attributed to isatin-hydrazine product formation, was frequently observed during soaks.

DISCUSSION OF RESULTS

Initial experiments were performed using reaction cocktails that contained a single isatin and a single hydrazine. In these instances, product binding was observed. Previous studies (Bramson, H. N., et al., *J. Med Chem.*, 44, 4339–4358 (2001)) suggested that inhibitors derived from A5 (see FIG. 1 & Table 2) should possess a relatively high degree of potency due to the presence of the sulphonamide group at the R$^{3}$ position in the ligand. A reaction cocktail containing B2 and (A1–A4) did not reveal ligand binding, suggesting that the chlorine substitutions at positions (R$^{1}$–R$^{3}$) did not confer significant potency upon the product ligands. A cocktail that contained B2+(A1–A6) did, however, reveal ligand binding; the electron density being consistent with product formed by the reaction of (B2+A5). Thus the (B2+A5) reaction product was preferentially selected from a set of six possible products, lending support to the notion that the R$^{3}$-sulphonamide group was conferring binding affinity upon the A5B2 ligand. The degeneracy of the product library was increased to 30 possible ligands using a reaction cocktail that contained isatins (B1–B5) and hydrazines (A1–A6). Each isatin was present at a concentration of 0.2 mM and each hydrazine at a concentration of 1.67 mM (see Table 3). Difference electron density consistent with the reaction product from (B2+A5) was again observed. These studies suggest that the protein preferentially selects the A5B2 ligand from the library of available product ligands. The potency of this compound was confirmed by synthesis of A5B2 ligand. It is known from the literature that compound A5B2 has an IC50 of 43 nM (Bramson, et al., 2001).

The invention claimed is:

1. A method for identifying a ligand of a target macromolecule comprising the steps of:
   a) soaking one or more crystals of the target macromolecule in a solution containing a collection of compounds generated in situ or separate from the crystal, where the solution has been prepared without the purification of the synthesized collection of compounds;
   b) obtaining an X-ray crystal diffraction pattern of the soaked macromolecule crystal; and
   c) using said X-ray crystal diffraction pattern to identify any compound bound to the macromolecule crystal, said compound being a ligand of the target macromolecule.

2. A method according to claim 1, wherein the target macromolecule is selected from the group consisting of: proteins, ribose nucleic acids, deoxy ribose nucleic acid, and complexes of combinations of these.

3. A method according to claim 2, wherein the target macromolecule is a protein.

4. A method according to claim 1, wherein the collection of compounds are synthesised individually and then mixed together.

5. A method according to claim 1, wherein the collection of compounds are synthesised as a mixture by combinatorial chemistry.

6. A method according to claim 1, wherein the members of the collection of compounds are present at a concentration of at least 10 times their $K_i$.

7. A method according to claim 1, wherein the amount of each compound being a member of the collection of compounds, present in the solution will be present at a concentration which is at least 10 times as much as the concentration of the target macromolecule in the reaction system.

8. A method according to of claim 1, wherein the members of the collection of compounds do not bind covalently to the target macromolecule.

9. A method for identifying a ligand of a target macromolecule comprising the steps of:
   a) synthesizing a collection of compounds, which are suitable for screening against a target macromolecule, in a solution containing one or more crystals of the target macromolecule;
   b) obtaining an X-ray crystal diffraction pattern of the soaked macromolecule crystal; and
   c) using said X-ray crystal diffraction pattern to identify any compound bound to the macromolecule crystal, said compound being a ligand of the target macromolecule.

10. A method for identifying a ligand of a target macromolecule comprising the steps of:
    a) synthesizing a collection of unpurified compounds, which are suitable for screening against a target macromolecule;
    b) adding the collection of compounds to a solution containing one or more crystals of the target macromolecule;
    c) obtaining an X-ray crystal diffraction pattern of the soaked macromolecule crystal; and
    d) using said X-ray crystal diffraction pattern to identify any compound bound to the macromolecule crystal, said compound being a ligand of the target macromolecule.

11. A method according to claim 10, wherein if step a) takes place in a solvent which is not compatible with the macromolecule crystals, then the method comprises the further step after step a) of separating the collection of compounds from the solvent in which the compounds were synthesised.

12. A method according to claim 10, wherein if step a) takes place in a solvent which is not compatible with the macromolecule crystals, the solvent in which step a) takes place is separated from the solution containing the one or more macromolecule crystals by a permeable membrane.

* * * * *